US00PP26197P2

(12) United States Plant Patent
Stemkens

(10) Patent No.: US PP26,197 P2
(45) Date of Patent: Dec. 8, 2015

(54) *ERYSIMUM* PLANT NAMED 'ERFZ0001'

(50) Latin Name: *Erysimum linifolium*
Varietal Denomination: ERFZ0001

(71) Applicant: SYNGENTA CROP PROTECTION AG, Basel (CH)

(72) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 121 days.

(21) Appl. No.: 13/986,953

(22) Filed: Jun. 18, 2013

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

(56) References Cited

PUBLICATIONS

PLUTO Plant Variety Database p. 1 Jan. 28, 2015.*

* cited by examiner

*Primary Examiner* — Annette Para
(74) *Attorney, Agent, or Firm* — Joshua L. Price

(57) ABSTRACT

A new *Erysimum* plant named 'ERFZ0001' particularly distinguished by the purple-violet flower color, medium green foliage color, rounded and compact plant habit with good branching and is early to flower.

1 Drawing Sheet

Latin name of the genus and species of the plant claimed: *Erysimum linifolium.*

Varietal denomination: 'ERFZ0001'.

BACKGROUND OF THE NEW PLANT

The present invention comprises a new *Erysimum*, botanically known as *Erysimum linifolium,* and hereinafter referred to by the variety name 'ERFZ0001'.

'ERFZ0001' is a product of a planned breeding program. The new cultivar 'ERFZ0001' has purple-violet flower color, medium green foliage color, rounded and compact plant habit with good branching, and is early to flower.

'ERFZ0001' originates from a hybridization made in a greenhouse in April 2009 in Enkhuizen, The Netherlands. The female parent was a commercially available plant identified as 'Bowles Mauve', unpatented, with mauve flower color, fewer branches, and overall larger size than that of 'ERFZ0001'.

The male parent of 'ERFZ0001' was an unpatented, proprietary plant identified as 'M1702-82' with dark lilac flower color, is later to flower and less vigorous than that of 'ERFZ0001'. The resultant seed was sown in September 2009 in a greenhouse, in Enkhuizen, The Netherlands.

'ERFZ0001' was selected as one flowering plant within the progeny of the stated cross in April 2010 in Enkhuizen, The Netherlands.

The first act of asexual reproduction of 'ERFZ0001' was accomplished when vegetative cuttings were propagated from the initial selection in the April 2010 in a controlled environment in Enkhuizen, The Netherlands.

BRIEF SUMMARY OF INVENTION

Horticultural examination of plants grown from cuttings of the plant initiated in April 2010 in Enkhuizen, The Netherlands, and continuing thereafter, has demonstrated that the combination of characteristics as herein disclosed for 'ERFZ0001' are firmly fixed and are retained through successive generations of asexual reproduction.

'ERFZ0001' has not been observed under all possible environmental conditions. The phenotype may vary significantly with variations in environment such as temperature, light intensity, and day length.

Plant Breeder's Right for this cultivar were applied for at the Community Plant Variety Office on Oct. 25, 2012 (2012/2346) and in Canada on Apr. 19, 2013 (13-7998). 'ERFZ0001' has not been made publicly available more than one year prior to the filing of this application.

The following traits have been repeatedly observed and are determined to be basic characteristics of the new variety. The combination of these characteristics distinguishes this *Erysimum* as a new and distinct variety

BRIEF DESCRIPTION OF THE PHOTOGRAPHS

The accompanying photographic drawing shows typical flower and foliage characteristics of 'ERFZ0001' with colors being as true as possible with an illustration of this type.

Figure 2:
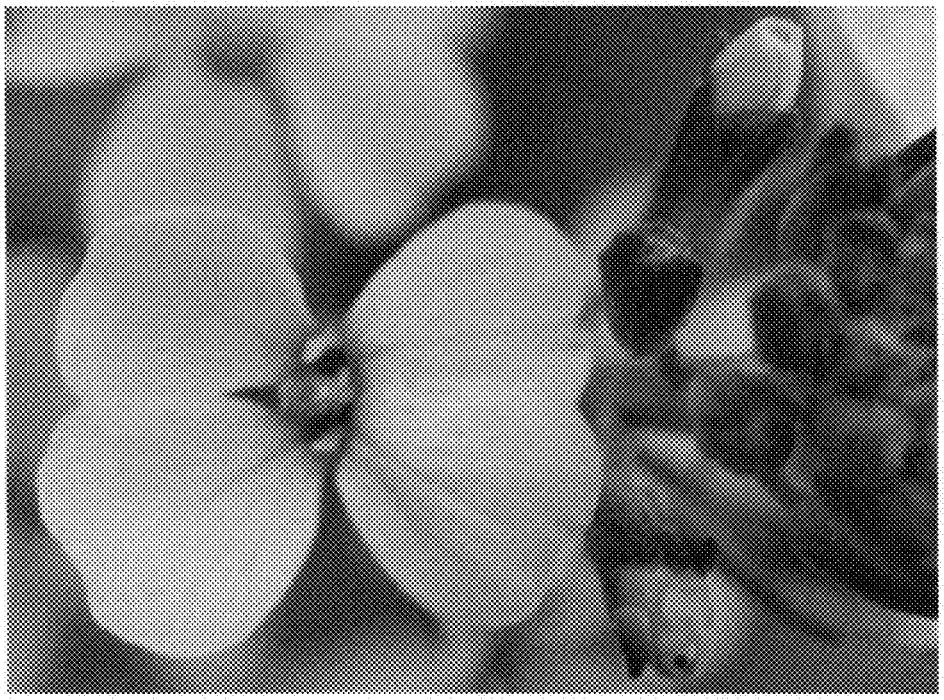
Figure 1:
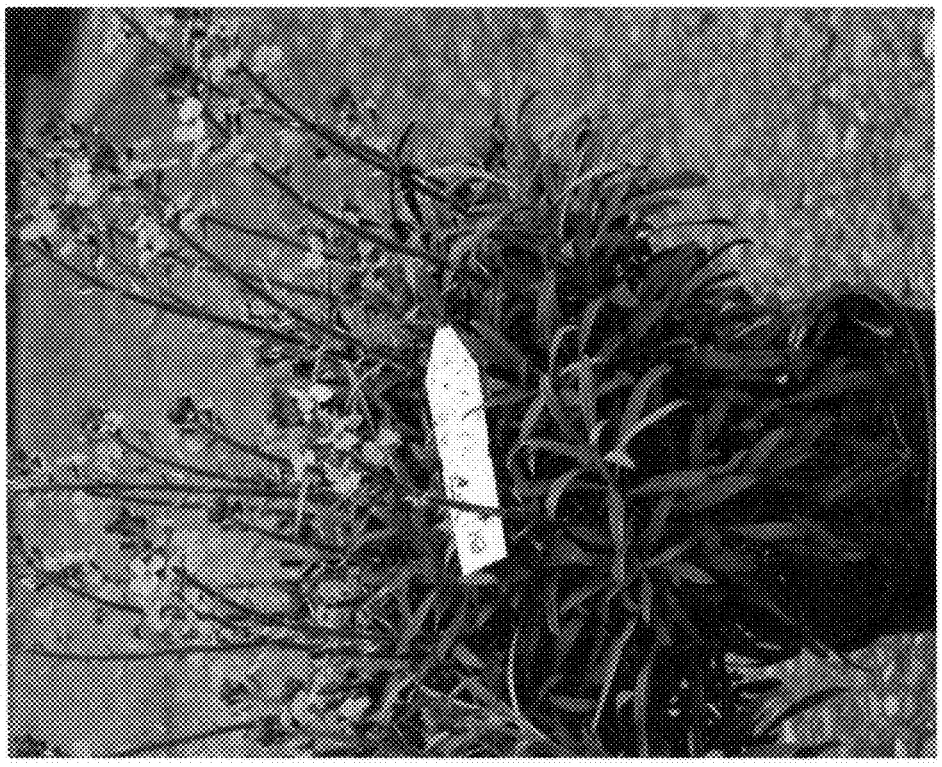

The photographic drawing shows in FIG. 1 a flowering plant of the new variety and in FIG. 2 a close-up of a flower and buds.

DETAILED BOTANICAL DESCRIPTION

The plant descriptions, measurements and aforementioned photographs were taken in Gilroy, Calif. in March 2013 under natural light. These plants were growing in an outdoor trial under natural light in Gilroy Calif. The plants were about 24 weeks of age.

Color chart used: Royal Horticultural Society Colour Chart (R.H.S.) 2001

TABLE 1

DIFFERENCES BETWEEN THE NEW VARIETY 'ERFZ0001' AND A SIMILAR VARIETY

| | 'ERFZ0001' | 'Bowles Mauve (Unprotected) |
|---|---|---|
| Natural flowering response: | Earlier | Later |
| Plant habit: | Somewhat more compact when plants start to flower | Not as compact |
| Foliage color: | Slightly greener | Little less green |
| Peduncle length: | Becomes longer on mature plants | Shorter |

Plant:

*Form, growth and habit.*—Compact and tightly mounded, good flowering on somewhat long peduncles at more mature stage.

*Plant height.*—28-30.0 cm.

*Plant height (inflorescence included).*—50-55.0 cm.

*Plant width.*—About 30.0 cm.

Roots:

*Number of days to initiate roots.*—About 8 days at about 18 degrees C.

*Number of days to produce a rooted cutting.*—About 4 weeks at 18 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 147A but lighter.

*Immature, leaf color, lower surface.*—Closest to RHS 137A.

*Mature, leaf color, upper surface.*—Closest to RHS 147A but lighter.

*Mature, leaf color, lower surface.*—Closest to RHS 137A.

*Length.*—6.5-6.8 cm.

*Width.*—1.0-1.2 cm.

*Shape.*—Narrowly oblanceolate to ensiform.

*Base shape.*—Cuneate.

*Apex shape.*—Acute to abruptly acute.

*Margin.*—Entire.

*Texture, upper surface.*—Bifid T-shaped hairs.

*Texture, lower surface.*—Bifid T-shaped hairs.

*Color of veins, upper surface.*—RHS 144B.

*Color of veins, lower surface.*—RHS 144B.

*Veination pattern.*—Pinnate.

*Petiole color.*—RHS 144B.

*Length.*—0.5-0.9 cm.

*Diameter.*—0.25 cm.

*Texture.*—Bifid T-shaped hairs.

Stem:

*Color of stem.*—RHS 144B but appears greyer due to hairs.

*Length of stem.*—13-15.0 cm.

*Diameter.*—0.45 cm.

*Length of internodes.*—0.5 cm.

*Texture.*—Bifid T-shaped hairs.

*Color of peduncle.*—RHS 144B.

*Length of peduncle.*—6.0-27.0 cm for the most mature.

*Diameter of peduncle.*—0.3-0.4 cm.

*Texture.*—Bifid T-shaped hairs.

*Color of pedicel.*—RHS 144B.

*Length of pedicel.*—0.4 cm.

*Diameter of pedicel.*—0.05 cm.

*Texture.*—Heavy covered with bifid T-shaped hairs.

Inflorescence:

*Type.*—Single, cruciform, composed of 4 petals; flowers held above the plant, relatively long peduncles on more mature plants.

*Natural flowering season.*—March to October in California.

*Quantity of inflorescences per plant.*—23-25 with open flowers and 20-25 immature ones.

*Lastingness of individual blooms on the plant.*—About 4 days.

*Fragrance.*—None.

Bud (just before opening/showing color):

*Color.*—Some RHS 155C and some closer to RHS 84C.

*Length.*—1.3 cm.

*Width.*—0.4-0.5 cm.

*Shape.*—Oblong.

Corolla:

*Immature inflorescence.*—Diameter: 1.2-1.4 cm. Color of petals, upper surface: Between RHS N81A and RHS N81B. Color of petals, lower surface: Closest to RHS N81B.

*Mature inflorescence.*—Flower diameter: 1.4-1.6 cm. Depth: 1.2-1.4 cm. Petal color, upper surface: Closest to RHS N81C. Petal color, lower surface: Closest to RHS N81C to RHS N81D. Length of petal: 0.7-0.8 cm. Width of petal: 0.8-0.9 cm. Shape: Spathulate. Apex shape: Slightly retuse. Petal base: Acuminate. Margin: Entire. Petal texture, upper surface: Papillose. Petal texture, lower surface: Papillose.

Calyx:

*Quantity.*—4 sepals.

*Color, upper surface.*—Closest to RHS 137B.

*Color, lower surface.*—Closest to RHS 137A heavily infused with anthocyanins of shades of about RHS N187A at the apex especially at the time the bud is opening; and the base closer to RHS 186C to RHS 186D.

Sepals:

*Length.*—0.7 cm.

*Width.*—0.3 cm.

*Shape.*—Broadly oblong.

*Apex shape.*—Obtuse.

*Base.*—Cuneate.

*Margins.*—Entire, though becoming slightly papery.

*Texture, upper/inner surface.*—Glabrous.

*Texture, lower/outer surface.*—Bifid T-shaped hairs.

Reproductive organs:

*Gynoecium.*—Pistil quantity: 1. Length: 0.6 cm. Style color: RHS 145B. Style length: 0.45-0.5 cm. Style texture: Heavily covered with bifid hairs as to appear much lighter in color. Stigma color: RHS 145B. Stigma shape: Oval to disc-shaped and a cleft down the center. Stigma texture: Very grainy looking. Ovary color: Not developed enough at this to observe.

*Androecium.*—Stamens, quantity: 6. Color of filaments: Closest to RHS 160D and somewhat translucent. Length filaments: 0.6 cm. Anther color: Closest to RHS 18C. Anther length: 0.3 cm. Anther shape: Oblong. Color of pollen: RHS 18C. Pollen amount: Normal.

Fertility/seed set: No seed set.

Disease/pest resistance: Has not been observed.

What is claimed is:

1. A new and distinct variety of *Erysimum* plant named 'ERFZ0001' substantially as illustrated and described herein.

* * * * *